United States Patent [19]

Tahara et al.

[11] Patent Number: 4,616,009

[45] Date of Patent: * Oct. 7, 1986

[54] NEUROLEPTIC INDOLE-3-CARBOXAMIDE DERIVATIVES

[75] Inventors: Tetsuya Tahara, Oita; Takemi Fukuda, Fukuoka; Michihide Setoguchi, Oita, all of Japan

[73] Assignee: Yoshitomi Pharmaceutical Industries, Ltd., Osaka, Japan

[*] Notice: The portion of the term of this patent subsequent to Mar. 18, 2003 has been disclaimed.

[21] Appl. No.: 679,437

[22] Filed: Dec. 7, 1984

[30] Foreign Application Priority Data

Dec. 8, 1983 [JP] Japan .................................. 58-232514

[51] Int. Cl.[4] .................. A61K 31/55; C07D 401/12; C07D 403/12
[52] U.S. Cl. .................................. 514/212; 540/602; 514/323; 514/414; 546/201; 548/467
[58] Field of Search .................. 546/201; 548/467; 260/245.7; 514/212, 323, 414

[56] References Cited

U.S. PATENT DOCUMENTS

| | | | |
|---|---|---|---|
| 3,136,770 | 6/1964 | Gray | 546/201 |
| 3,527,761 | 9/1970 | Archibald et al. | 546/201 |
| 4,140,691 | 2/1979 | Weston et al. | 546/201 |

FOREIGN PATENT DOCUMENTS

| | | | |
|---|---|---|---|
| 1173148 | 2/1959 | France | 546/201 |
| 1255928 | 2/1961 | France | 546/201 |
| 1273563 | 5/1972 | United Kingdom | 546/201 |
| 1345872 | 2/1974 | United Kingdom | 546/201 |

OTHER PUBLICATIONS

Archibald, J. L., et al., *Journal of Medicinal Chemistry*, vol. 14, No. 11, 1971, pp. 1054–1059.

*Primary Examiner*—Richard A. Schwartz
*Attorney, Agent, or Firm*—Sughrue, Mion, Zinn, Macpeak and Seas

[57] ABSTRACT

Indole-3-carboxamide derivatives of the formula:

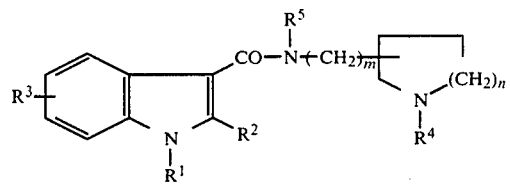

inclusive of pharmaceutically acceptable acid addition salt and/or hydrate forms thereof, wherein $R^1$ is hydrogen, $C_{1-4}$ alkyl, phenyl which may be optionally substituted by halogen on the benzene ring or phenyl-$C_{1-4}$ alkyl which may be optionally substituted by halogen on the benzene ring; $R^2$ is hydrogen or $C_{1-4}$ alkyl; $R^3$ is hydrogen, halogen, $C_{1-4}$ alkyl, hydroxy or $C_{1-4}$ alkoxy; $R^4$ is hydrogen, $C_{1-4}$ alkyl, $C_{3-7}$ cycloalkyl, allyl or benzyl which may be optionally substituted by halogen on the benzene ring or by methyl on the α-carbon; $R^5$ is hydrogen or $C_{1-4}$ alkyl; m is 0 or 1; and n is an integer of 1 to 3, are useful as neuroleptic and anxiolytic drugs, and for the prevention and treatment of psychosomatic disturbances.

8 Claims, No Drawings

NEUROLEPTIC INDOLE-3-CARBOXAMIDE DERIVATIVES

FIELD OF THE INVENTION

The present invention relates to novel and therapeutically valuable indole-3-carboxamide derivatives, pharmaceutically acceptable acid addition salts thereof and hydrates thereof, method for preparing the indole-3-carboxamide derivatives and pharmaceutical compositions containing at least one indole-3-carboxamide derivative.

BACKGROUND OF THE INVENTION

Benzamide compounds represented by sulpiride has been used as antischizophrenic drugs, and are well known to have less side effects on the extrapyramidal system and weak cataleptogenic activity unlike butyrophenone compounds such as haloperidol or phenothiazine compounds such as chlorpromazine. Sulpiride, however, is also reported to have a low bioavailability in oral administration and poor penetration across blood-brain barrier. Sulpiride is also used as anti-ulcer agents.

U.S. Pat. No. 3,527,761 or *Journal of Medicinal Chemistry*, Vol. 14, p. 1054 (1971) decribes 3-indoleethylamine compounds possessing mainly antihypertensive activity, and in particular, 3-{2-[4-(3-indolecarboxamido)-piperidino]ethyl}indole having antihypertensive and antihistaminic activities. Among these 3-indoleethylamine compounds, indoramin (INN, 3-[2-(4-benzamido-1-piperidyl)-ethyl]indole) is selected as the compound having stronger antihypertensive activity, and also exhibits antihistaminic activity and anticonvulsant activity. According to studies of the present inventors, indoramin shows weak apomorphine-antagonistic activity, but it cannot be used as neuroleptic and anxiolytic drugs because of exhibition of relatively strong antihypertensive activity. Other known 3-indoleethylamine compounds mentioned above do not show apomorphine-antagonistic activity, in practice.

Since benzamide compounds have dopamine-antagonistic activity as a main activity, the present inventors have synthesized a series of compounds in place of the phenyl moiety of the benzamide compounds into indole moiety which is the nucleus of serotonin, and investigated their pharmacological activities.

SUMMARY OF THE INVENTION

As a result of such intensive investigations, the present inventors have found that novel indole-3-carboxamide derivatives, pharmaceutically acceptable acid addition salts thereof and hydrates thereof have excellent oral uptake and blood-brain barrier permeability, and potent anti-dopamine action with higher selectivity to the mesolimbic system, and further serotonin- and noradrenaline-antagonistic activities, and are useful as neuroleptic and anxiolytic drugs, and for the prevention and treatment of psychosomatic disturbances such as gasteric ulcer and duodenal ulcer.

DETAILED DESCRIPTION OF THE INVENTION

The indole-3-carboxamide derivatives of the present invention are represented by the following formula:

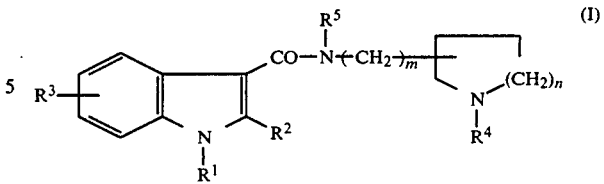

wherein $R^1$ is a hydrogen atom, a $C_{1-4}$ alkyl group, a phenyl group which may be optionally substituted by a halogen atom or the benzene ring or a phenyl-$C_{1-4}$ alkyl group which may be optionally substituted by a halogen atom on the benzene ring; $R^2$ is a hydrogen atom or a $C_{1-4}$ alkyl group; $R^3$ is a hydrogen atom, a halogen atom, a $C_{1-4}$ alkyl group, a hydroxyl group, a $C_{1-4}$ alkoxy group; $R^4$ is a hydrogen atom, a $C_{1-4}$ alkyl group, a $C_{3-7}$ cycloalkyl group, an allyl group or a benzyl group which may be optionally substituted by a halogen atom on the benzene ring or by a methyl group on the α-carbon atom; $R^5$ is a hydrogen atom or a $C_{1-4}$ alkyl group; m is 0 or 1; and n is an integer of 1 to 3.

In the above definitions, a $C_{1-4}$ alkyl group means methyl, ethyl, propyl, isopropyl, butyl or tertiary butyl; a halogen atom means fluorine, chlorine, bromine or iodine; a $C_{1-4}$ alkoxy group means methoxy, ethoxy, propoxy or butoxy; and a $C_{3-7}$ cycloalkyl group means cyclopropyl, cyclobutyl, cyclopentyl, cyclohexyl or cycloheptyl.

The compounds of formula (I) can be, for example, prepared by the following processes of:

(1) reacting a compound of the formula:

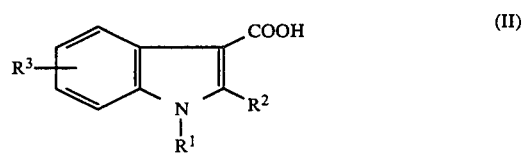

wherein each symbol is as defined above, or a functional derivative thereof with a compound of the formula:

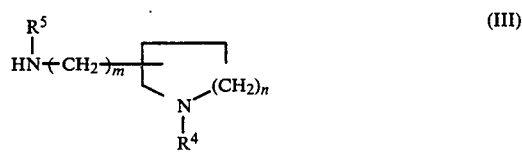

wherein each symbol is as defined above with the proviso that $R^4$ is other than a hydrogen atom;

(2) treating a compound of the formula:

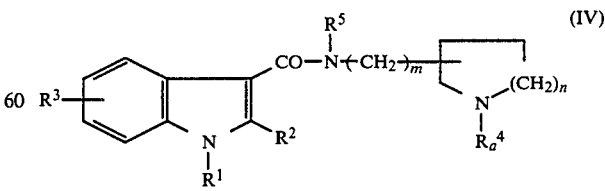

wherein $R_a^4$ is a methyl group or a benzyl group and other symbols are as defined above, with hydrobromic acid;

(3) subjecting a compound of the formula:

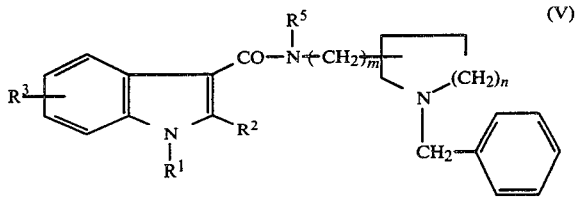

wherein each sumbol is as defined above, to catalytic hydrogenation;

(4) reacting a compound of the formula:

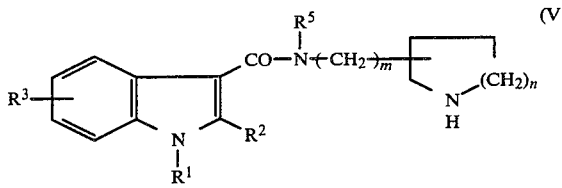

wherein each symbol is as defined above, with a compound of the formula:

$$R_b{}^4-X \qquad (VII)$$

wherein $R_b{}^4$ is as defined in $R^4$ except a hydrogen atom and X is a reactive atom or group such as a halogen atom (e.g., chlorine, bromine or iodine), an alkanesulfonyloxy group (e.g., methanesulfonyloxy) or an arenesulfonyloxy group (e.g., benzenesulfonyloxy or p-toluenesulfonyloxy);

(5) reacting a compound of the formula:

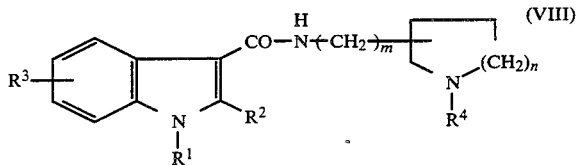

wherein each symbol is as defined above, with an alkylating agent.

The reaction of process (1) is carried out by a conventional amide preparation method or a peptide synthesis method.

In case the compounds of formula (II) is carboxylic acids, for example, the reaction is carried out in an inert solvent at room temperature or under cooling or heating in the presence of a condensing agent such as a carbodiimide (e.g., dicyclohexylcarbodiimide), titanium tetrachloride, a phosphorus halide (e.g., phosphorus trichloride or phosphorus oxychloride), diphenylphosphoryl azide or a quaternary pyridinium salt (e.g., 2-chloro-N-methylpyridinium iodide or 3-methanesulfonyloxy-N-methylpyridinium iodide).

When an acid halide (e.g., an acid chloride or an acid bromide) or a mixed acid anhydride (e.g., a mixed acid anhydride with a carbonic acid hemi lower alkyl ester, a lower alkanoic acid or a mixed acid anhydride with a lower alkylphosphoric acid) is used as the functional derivative of the carboxylic acids of formula (II), the reaction is carried out in an inert solvent at room temperature, or under cooling or heating, preferably in the presence of a deacidifying agent such as an organic base (e.g., triethylamine or pyridine) or an inorganic base (e.g., sodium hydrogencarbonate, an alkali carbonate or an alkali hydroxide).

In case an active ester (e.g., p-nitrophenyl ester, p-nitrobenzyl ester or p-chlorophenyl ester) is used as other functional derivative, the reaction is carried out in an inert solvent at room temperature or under refluxing, if desired, in the presence of a strong basic catalyst like sodium alkoxide.

The compounds of formula (II) wherein $R^3$ is a hydroxyl group may be used by means of the protection of the hydroxyl group with a lower alkoxy group, a benzyloxy group, a lower alkanoyloxy group, a benzoyloxy group or a dihydropyranyloxy group for acylation of the compounds of formula (III) as mentioned above. And then the protecting group of the resulting compounds can be removed by treating with an acid or alkali or subjecting to catalytic hydrogenation on palladium carbon or platinum oxide and so on, if desired.

According to processes (2) and (3), the compounds of formula (I) wherein $R^4$ is a hydrogen atom can be obtained. The reaction of process (2) is preferably carried out in acetic acid, and the reaction of process (3) is carried out in an inert solvent in the presence of a catalyst such as palladium carbon, Raney nickel or platinum oxide.

The alkylating agent employed in process (5) includes a lower alkyl halide or an ester of a lower alkanol with p-toluenesulfonic acid, methanesulfonic acid or sulfuric acid. The alkylating reaction is usually carried out after treating the compounds of formula (VIII) with sodium hydride or sodium amide in an inert solvent.

Any inert solvent can be used in practicing the above reaction, and preferably water, a lower alkanol (e.g., methanol, ethanol, or isopropanol), an ester (e.g., ethyl acetate), an aromatic hydrocarbon (e.g., benzene or toluene), a halogenated hydrocarbon (e.g., methylene chloride or chloroform), a ketone (e.g., acetone or methyl ethyl ketone), an ether (e.g., diethyl ether, tetrahydrofuran or dioxane), dimethylformamide or dimethyl sulfoxide, or a mixture thereof are used.

The compounds of the present invention are prepared as a racemate by using the starting compounds having a chiral carbon atom. The present invention also embraces individual optically active isomers. The optically active compounds of formula (I) can, if desired, be prepared by resolving the resulting racemate in a conventional manner with an optically active acid (e.g., tartaric acid, dibenzoyltartaric acid, mandelic acid or 10-camphorsulfonic acid) or by using the optically active compounds previously prepared as a starting compound.

The compounds of the present invention can, if desired, be converted into pharmaceutically acceptable acid addition salts thereof in a conventional manner by treating with an inorganic acid (e.g., hydrochloric acid, hydrobromic acid, phosphoric acid, nitric acid or sulfuric acid) or an organic acid (e.g., p-toluenesulfonic acid, methanesulfonic acid, citric acid, butyric acid, maleic acid, fumaric acid or tartaric acid).

The compounds of formula (I), pharmaceutically acceptable acid addition salts thereof and hydrates thereof exhibit potent anti-dopamine activity as shown in the following pharmacological experiment, but do not show antihypertensive activity or antihistaminic activity, and are useful as neuroleptic drugs without extrapyramidal side effect and the other undesirable adverse effects such as hypotension.

Antiapomorphine Activity in Mice

Groups of 5 male dd-strain mice were used. Test compounds were orally or intraperitoneally administered and 60 minutes thereafter, 0.5 mg/kg of apomorphine hydrochloride was subcutaneously administered. Immediately thereafter, spontaneous motility of the mice was measured with the aid of Animex (manufactured by Columbus Company, U.S.A.) for 20 minutes. The procedure was repeated three times with respective groups. The dose of test compounds required for 50% suppression of spontaneous motility of control group was graphically intraporated and determined as $ED_{50}$ value. The results are shown in Table 1.

TABLE 1

| Test Compound | Antiapomorphine Activity $ED_{50}$ (mg/kg) | Route |
|---|---|---|
| Example 1 | 17.0 | p.o. |
| Example 2 | 4.6 | p.o. |
| Example 3 | 9.5 | p.o. |
| Example 4 | 27.0 | p.o. |
| Example 7 | 8.7 | p.o. |
| Example 8 | 7.0 | p.o. |
| Example 9 | 30.0 | p.o. |
| Example 10 | 10.0 | i.p. |
| Example 12 | 5.6 | p.o. |
| Example 13 | 5.6 | p.o. |
| Example 14 | 5.2 | p.o. |
| Example 18 | 24.0 | p.o. |
| Sulpiride | 330.0 | p.o. |

The acute toxicity of the compounds of the present invention was studied in 5 male mice weighing 30 to 45 g. The mice were observed for 5 days after the oral administration of the test compound, and the mortality was calculated. All animals were survived even at the dose of 500 mg/kg of compound of Example 2.

In view of various tests including those mentioned above, the compounds of the invention represented by formula (I), in base or salt form, can be safely administered as neuroleptic and anxiolytic drugs, and for the prevention and treatment of psychosomatic disturbances, in the form of a pharmaceutical preparation with a suitable and conventional pharmaceutically acceptable carrier, without adversely affecting the patients.

The pharmaceutical preparation can take any conventional form such as tablets, capsules, granules, powders or injectable solutions.

The following is an example of formulations when a compound of the invention is administered for pharmaceutical purposes:

Tablets (30 mg) are prepared from the following compositions:

| | |
|---|---|
| Compound 2 | 30.0 mg |
| Lactose | 50.0 mg |
| Microcrystalline Cellulose | 16.0 mg |
| Corn Starch | 10.0 mg |
| Talc | 3.0 mg |
| Magnesium Stearate | 1.0 mg |
| | 110.0 mg |

The single dose of the compound of the invention for human adults usually ranges from about 0.1 mg/kg to about 10 mg/kg, but it may vary depending upon the age, body weight, and/or severity of the conditions to be treated as well as the response to the medication.

The present invention will be better understood from the following examples, but they are not to be construed as limiting the present invention.

EXAMPLE 1

To a solution of 8 g of 2-methylindolecarboxylic acid and 6 g of 1-ethyl-2-pyrrolidinylmethylamine in 140 ml of tetrahydrofuran was added 9.5 g of dicyclohexylcarbodiimide, and the whole mixture was refluxed under heating for 1.5 hours. After cooling, the precipitated dicyclohexylurea was filtered off and the filtrate was concentrated. The resulting residue was crystallized with 20 ml of ethyl acetate and the crystals were filtered with suction and then recrystallized from ethyl acetate to give 10 g of N-(1-ethyl-2-pyrrolidinylmethyl)-2-methylindole-3-carboxamide as white crystals, melting at 132°–135° C.

EXAMPLE 2

To a solution of 16 g of 5-fluoro-2-methylindole-3-carboxylic acid in 260 ml of tetrahydrofuran were added 16 g of 4-amino-1-benzylpiperidine and 19 g of dicyclohexylcarbodiimide, and the whole mixture was refluxed under heating for 3 hours. After cooling, the precipitated dicyclohexylurea was filtered off and the extract was concentrated. A mixture of the residue in 70 ml of tetrahydrofuran was stirred at room temperature and the insoluble dicyclohexylurea was filtered off. The filtrate was concentrated and the resulting residue was crystallized with hexane. The resultant crystals were filtered with suction and recrystallized from ethyl acetate to give 22.5 g of N-(1-benzyl-4-piperidyl)-5-fluoro-2-methylindole-3-carboxamide, melting at 166°–169° C.

EXAMPLE 3

To a solution of 5.1 g of 5-fluoroindole-3-carboxylic acid in 150 ml of tetrahydrofuran were added 5.5 g of 4-amino-1-benzylpiperidine and 5.8 g of dicyclohexylcarbodiimide, and the whole mixture was refluxed under heating on a water bath for 3 hours. After completion of the reaction, the precipitated dicyclohexylurea and a part of the objective product were filtered and suspended in 200 ml of hot tetrahydrofuran. The suspension was stirred and the insoluble dicyclohexylurea was filtered off with suction. The combined filtrates were concentrated and the residue was crystallized with ethyl acetate. The resulting crystals were filtered to give 8.3 g of N-(1-benzyl-4-piperidyl)-5-fluoroindole-3-carboxamide. The product, when recrystallized from a mixture of ethyl acetate and ethanol, melts at 215°–217° C.

EXAMPLE 4

To a suspension of 2.5 g of 5-fluoro-1,2-dimethylindole-3-carboxylic acid in 40 ml of benzene was added 3 g of thionyl chloride, and the resulting mixture was refluxed under heating for 4 hours. After cooling, the reaction mixture was concentrated under reduced pressure and hexane was added to the residual oil. The precipitated acid chloride was filtered and added to a solution of 5 g of 4-amino-1-benzylpiperidine in 100 ml of benzene under cooling. The mixture was stirred at room temperature for an hour and then refluxed for an hour. After the precipitated amine compound as hydrochloride was filtered off, the filtrate was washed with water. The organic layer was separated and dried and then concentrated. The residue was crystallized with isopropyl ether and resulting crystals were filtered with suction and recrystallized from ethyl acetate to give N-(1-benzyl-4-piperidyl)-5-fluoro-1,2-dimethylindole-3-carboxamide, melting at 169°–172° C.

EXAMPLE 5

To 30 ml of ethyl acetate were added 1.5 g of 1-benzyl-5-fluoro-2-methylindole-3-carboxylic acid and then 0.8 ml of thionyl chloride, and the whole mixture was refluxed under heating for 3 hours. After concentration, to a solution of the residue in 80 ml of ethyl acetate were added 1 ml of pyridine and 1.1 g of 4-amino-1-benzylpiperidine, and the mixture was stirred at room temperature for 2 hours. After cooling, the precipitated crystals were filtered and the mother liquor was concentrated. The residue was crystallized from a small amount of ethyl acetate and the resulting crystals were filtered. 2.3 g of the combined crystals were dissolved in methanol and made alkaline with an ammonia solution. The resulting crystals were filtered and recrystallized from methanol to give 1-benzyl-N-(1-benzyl-4-piperidinyl)-5-fluoro-2-methylindole-3-carboxamide, melting at 194°–195° C.

EXAMPLE 6

To a solution of 9 g of N-(1-benzyl-4-piperidyl)-1-butyl-5-hydroxy-2-methylindole-3-carboxamide in 100 ml of methanol were added 5 g of an 18% hydrochloric acid in ethanol and 4 g of 10% palladium carbon, and the mixture was subjected to catalytic hydrogenation at atmospheric pressure for 6 hours. After the catalyst was filtered off, the filtrate was concentrated under reduced pressure. The residue was crystallized with ethyl acetate and the resulting crystals were recrystallized from ethanol to give 4 g of 1-butyl-5-hydroxy-2-methyl-N-(4-piperidyl)indole-3-carboxamide hydrochloride, melting at 164°–168° C.

EXAMPLE 7

To a suspension of 1.2 g of 2-methyl-N-(4-piperidyl)indole-3-carboxamide and 1 g of potassium carbonate in 50 ml of toluene and 10 ml of dimethylformamide was added dropwise 0.6 g of benzyl chloride. The mixture was refluxed under heating for 3 hours. After cooling, 50 ml of water was poured into the mixture. The insoluble materials precipitated were filtered by suction and recrystallized from methanol to give N-(1-benzyl-4-piperidyl)-2-methylindole-3-carboxamide, melting at 150°–153° C.

The following indole-3-carboxamide derivatives can be prepared in a similar manner as above Examples:

(8) N-(1-Benzyl-4-piperidyl)indole-3-carboxamide, melting at 214°–216° C.
(9) 5-Chloro-N-(1-ethyl-2-pyrrolidinylmethyl)-2-methylindole-3-carboxamide, melting at 125°–128° C.
(10) N-(1-Ethyl-2-pyrrolidinylmethyl)-5-fluoro-2-methylindole-3-carboxamide, melting at 130°–132° C.
(11) N-(1-Benzyl-2-pyrrolidinylmethyl)-5-fluoro-2-methylindole-3-carboxamide, melting at 175°–178° C.
(12) N-(1-Benzyl-3-pyrrolidinyl)-5-fluoro-2-methylindole-3-carboxamide, melting at 162°–164° C.
(13) N-[1-(p-Chlorobenzyl)-4-piperidyl]-5-fluoro-2-methylindole-3-carboxamide, melting at 175°–178° C.
(14) 5-Fluoro-N-[1-(p-fluorobenzyl)-4-piperidyl]-2-methylindole-3-carboxamide, melting at 179°–182° C.
(15) 5-Fluoro-N-(1-isobutyl-4-piperidyl)-2-methylindole-3-carboxamide, melting at 169°–173° C.
(16) 5-Fluoro-2-methyl-N-(1-methyl-4-piperidyl)indole-3-carboxamide, melting at 175°–179° C.
(17) 5-Fluoro-2-methyl-N-[1-(α-methylbenzyl)-4-piperidyl]indole-3-carboxamide, melting at 192°–194° C.
(18) N-[1-(m-Chlorobenzyl)-4-piperidyl]-5-fluoro-2-methylindole-3-carboxamide, melting at 149°–152° C.
(19) N-[1-(o-Chlorobenzyl)-4-piperidyl]-5-fluoro-2-methylindole-3-carboxamide, melting at 187°–189° C.
(20) N-(1-Allyl-4-piperidyl)-5-fluoro-2-methylindole-3-carboxamide, melting at 150°–152° C.
(21) N-(1-Benzyl-4-piperidyl)-5-hydroxy-2-methylindole-3-carboxamide, melting at 229°–232° C. with decomposition
(22) N-(1-Benzyl-4-piperidyl)-2,5-dimethylindole-3-carboxamide, melting at 230°–233° C. with decomposition
(23) N-(1-Benzyl-4-piperidyl)-5-methoxy-2-methylindole-3-carboxamide, melting at 185°–188° C.
(24) N-(1-Benzyl-4-piperidyl)-5-fluoro-N,2-dimethylindole-3-carboxamide, hydrochloride, melting at 266°–268° C. with decomposition
(25) 5-Fluoro-N-(4-piperidyl)indole-3-carboxamide, melting at 235°–237° C.
(26) 5-Hydroxy-2-methyl-N-(4-piperidyl)indole-3-carboxamide monohydrate, melting at 190°–196° C. with decomposition
(27) N-(1-Cyclohexyl-2-pyrrolidinylmethyl)-5-fluoro-2-methylindole-3-carboxamide, melting at 159°–163° C.
(28) 5-Fluoro-N-(1-isobutyl-2-pyrrolidinylmethyl)-2-methylindole-3-carboxamide, melting at 156°–159° C.
(29) N-(1-Butyl-2-pyrrolidinylmethyl)-5-fluoro-2-methylindole-3-carboxamide, melting at 160°–163° C.
(30) N-(1-Benzyl-4-piperidyl)-5-fluoro-2-methyl-1-phenylindole-3-carboxamide, melting at 129°–131° C.
(31) N-(1-Benzyl-4-piperidyl)-5-fluoro-1-(p-fluorophenyl)-2-methylindole-3-carboxamide
(32) 5-Fluoro-2-methyl-N-(4-piperidyl)indole-3-carboxamide, melting at 206°–207° C.

Although the present invention has been adequately discussed in the foregoing specification and examples included therein, one readily recognizes that various changes and modifications may be made without departing from the spirit and scope thereof.

What is claimed is:
1. An indole-3-carboxamide derivative of the formula:

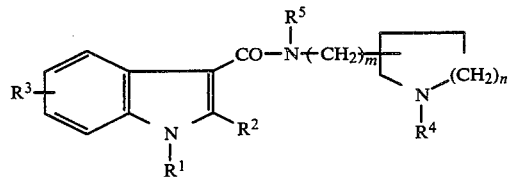

wherein $R^1$ is a hydrogen atom, a $C_{1-4}$ alkyl group, a phenyl group which may be optionally substituted by a halogen atom or a phenyl-$C_{1-4}$ alkyl group which may be optionally substituted by a halogen atom on the benzene ring; $R^2$ is a hydrogen atom or a $C_{1-4}$ alkyl group; $R^3$ is a hydrogen atom, a halogen atom, a $C_{1-4}$ alkyl group, a hydroxyl group, a $C_{1-4}$ alkoxy group; $R^4$ is a hydrogen atom, a $C_{1-4}$ alkyl group, a $C_{3-7}$ cycloalkyl group, an alkyl group or a benzyl group which may be optionally substituted by a halogen atom on the benzene ring or by a methyl group on the α-carbon; $R^5$ is a hydrogen atom or a $C_{1-4}$ alkyl group; m is 0 or 1; and n is an integer of 1 to 3, or a pharmaceutically acceptable acid addition salt or hydrate form thereof.

2. The compound of claim 1: N-(1-Benzyl-4-piperidyl)-5-fluoro-2-methylindole-3-carboxamide.

3. The compound of claim 1: N-(1-Benzyl-4-piperidyl)-5-fluoroindole-3-carboxamide.

4. The compound of claim 1: N-(1-Benzyl-4-piperidinyl)-2-methylindole-3-carboxamide.

5. The compound of claim 1: N-(1-Benzyl-4-piperidyl)indole-3-carboxamide.

6. The compound of claim 1: N-(1-Benzyl-3-pyrrolidinyl)-5-fluoro-2-methylindole-3-carboxamide.

7. The compound of claim 1: N-[1-(p-Chlorobenzyl)-4-piperidyl]-5-fluoro-2-methylindole-3-carboxamide.

8. A pharmaceutical composition comprising a neuroleptic, anxiolytic or psychosomatic disturbance treatment effective amount of the compound of claim 1 and a pharmaceutically acceptable carrier.

* * * * *